(12) United States Patent
Wake et al.

(10) Patent No.: US 11,375,879 B2
(45) Date of Patent: Jul. 5, 2022

(54) HOOD FOR ENDOSCOPE AND ENDOSCOPE SYSTEM

(71) Applicant: OLYMPUS CORPORATION, Tokyo (JP)

(72) Inventors: Fuminori Wake, Hachioji (JP); Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 305 days.

(21) Appl. No.: 16/672,619

(22) Filed: Nov. 4, 2019

(65) Prior Publication Data

US 2020/0060519 A1 Feb. 27, 2020

Related U.S. Application Data

(63) Continuation of application No. PCT/JP2018/016369, filed on Apr. 20, 2018.

(30) Foreign Application Priority Data

May 10, 2017 (JP) .............................. JP2017-094237

(51) Int. Cl.
*A61B 1/00* (2006.01)
*A61B 1/12* (2006.01)

(52) U.S. Cl.
CPC ...... *A61B 1/00089* (2013.01); *A61B 1/00091* (2013.01); *A61B 1/126* (2013.01); *A61B 1/00119* (2013.01)

(58) Field of Classification Search
CPC .. A61B 1/00089; A61B 1/00091; A61B 1/126
See application file for complete search history.

(56) References Cited

U.S. PATENT DOCUMENTS 4,436,087 A 3/1984 Ouchi
5,725,477 A * 3/1998 Yasui ................ A61B 1/00091
600/121

(Continued)

FOREIGN PATENT DOCUMENTS

EP 2305092 A1 4/2011
JP S54-107191 Z 7/1979

(Continued)

OTHER PUBLICATIONS

International Search Report dated Jun. 26, 2018 issued in PCT/JP2018/016369.

*Primary Examiner* — Matthew J Kasztejna
(74) *Attorney, Agent, or Firm* — Scully, Scott, Murphy & Presser, P.C.

(57) ABSTRACT

A hood for endoscope is attached to an endoscope including an insertion portion, a distal end portion and an air-feeding conduit, and the hood for endoscope includes a frame configured to be fitted to an outer circumference of the distal end portion, and a rectification plate configured to, so that gas spurted out forward in a longitudinal axis direction from an air-feeding port flows, changing an orientation in which the gas flows, from the longitudinal axis direction to a circumferential direction of the frame intersecting the longitudinal axis direction by the gas hitting the rectification member, guide the gas in a direction not toward a position of the distal end portion provided with an observation member.

13 Claims, 17 Drawing Sheets

(56) References Cited

U.S. PATENT DOCUMENTS

| | | | | |
|---|---|---|---|---|
| 6,508,810 | B1* | 1/2003 | Ouchi | A61B 1/00091 |
| | | | | 239/491 |
| 8,465,421 | B2* | 6/2013 | Finkman | A61B 1/015 |
| | | | | 600/156 |
| 8,491,467 | B2* | 7/2013 | Miyamoto | A61B 1/12 |
| | | | | 600/157 |
| 2001/0004692 | A1* | 6/2001 | Kidooka | A61M 3/0279 |
| | | | | 606/46 |
| 2007/0066870 | A1 | 3/2007 | Ohashi et al. | |
| 2007/0290073 | A1* | 12/2007 | Peterson | B05B 7/0416 |
| | | | | 239/399 |
| 2008/0058591 | A1* | 3/2008 | Saadat | A61B 1/018 |
| | | | | 600/109 |
| 2009/0253964 | A1* | 10/2009 | Miyamoto | A61B 1/126 |
| | | | | 600/157 |
| 2011/0054252 | A1 | 3/2011 | Ozaki et al. | |
| 2014/0371763 | A1 | 12/2014 | Poll et al. | |

FOREIGN PATENT DOCUMENTS

| | | |
|---|---|---|
| JP | 2001-321323 A | 11/2001 |
| JP | 2007-082766 A | 4/2007 |
| JP | 2011-045525 A | 3/2011 |
| JP | 2013-162863 A | 8/2013 |
| JP | 2013-165791 A | 8/2013 |
| WO | WO 2014/205140 A2 | 12/2014 |

* cited by examiner

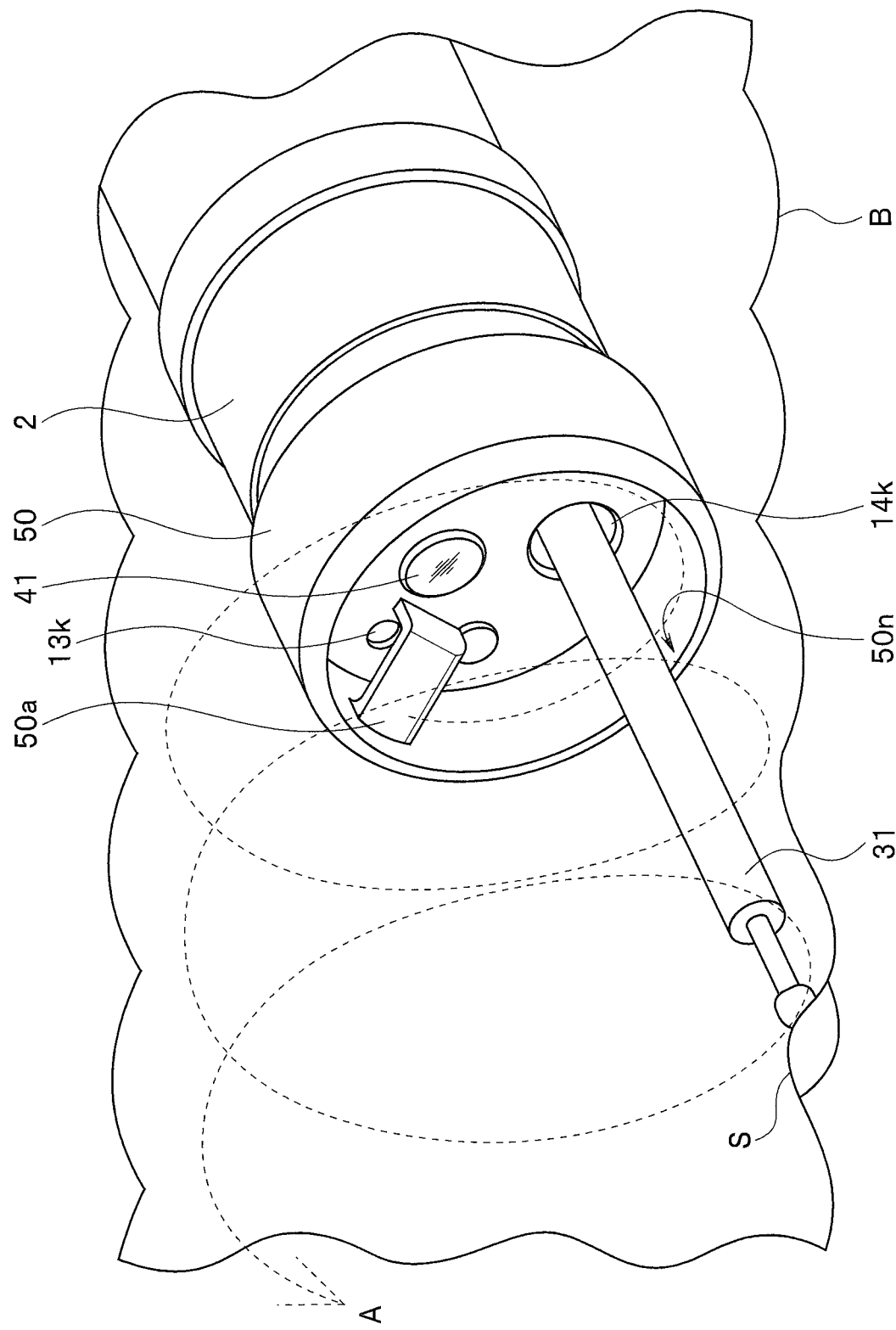

HOOD FOR ENDOSCOPE AND ENDOSCOPE SYSTEM

CROSS REFERENCE TO RELATED APPLICATION

This application is a continuation application of PCT/JP2018/016369 filed on Apr. 20, 2018 and claims benefit of Japanese Application No. 2017-094237 filed in Japan on May 10, 2017, the entire contents of which are incorporated herein by this reference.

BACKGROUND OF THE INVENTION

1. Field of the Invention

The present invention relates to a hood for endoscope attached to an endoscope, and an endoscope system.

2. Description of the Related Art

In an endoscope system provided with an endoscope used in a medical field, a cauterization treatment procedure is well known in which, by inserting an insertion portion of the endoscope into a living body to be a subject and, in a state in which treatment target tissue in biological tissue in the living body is being observed under endoscopic observation, causing a cauterization apparatus inserted into a treatment instrument insertion conduit via a treatment instrument insertion opening provided on an operation portion of the endoscope to project from an opening provided on the insertion portion and giving energy to the treatment target tissue from the projected cauterization apparatus, the treatment target tissue is detached and ablated from the biological tissue.

As an example, an ESD (endoscopic submucosal dissection) procedure in endoscopic treatment for removing a lesion site such as cancer tissue in a living body under endoscopic observation is well known.

More specifically, the ESD procedure is known, for example, as treatment in which an insertion portion of an endoscope is inserted into a living body, and by causing a cauterization apparatus, for example, a high-frequency knife inserted in a treatment instrument insertion conduit of the endoscope to project forward in a longitudinal axis direction from a distal end of the insertion portion and after that, causing the insertion portion to move back and forth in the longitudinal axis direction, in a state in which cancer tissue existing in the living body is included in an observation field of view of the endoscope, the cancer tissue caused to float by injection of dedicated liquid beforehand is removed using the high-frequency knife.

Note that, in the cauterization treatment procedure such as the ESD procedure, a configuration is well known in which a tubular hood for endoscope is attached on an outer circumference on a distal end side of the insertion portion, the hood being configured to keep a distance constant between an objective lens, which is an observation member, and treatment target tissue and at the time of turning over skin-like tissue of a lesion site on the treatment target tissue taken off, for example, with the high-frequency knife, prevent the skin-like tissue from covering the lesion site and cause the lesion site to be exposed.

Here, during a procedure like the ESD procedure in which living tissue is dissected and blood is coagulated, a mucous membrane and fat become fluid including solid particle components, more specifically, mist as gas including components derived from the living tissue, accompanying the dissection and the coagulation performed by applying a high-frequency current to cancer tissue, for example, from the high-frequency knife.

As a result, especially in a procedure requiring a long time period like the ESD procedure, the mist easily fills in a small space and easily adheres to the objective lens. Therefore, such a situation may occur that the observation field of view of the endoscope is blocked and is unclear.

Therefore, in order to secure the observation field of view during the ESD procedure, it is desirable to use a method of taking in gas including the components derived from the living tissue from an air intake port using an air intake conduit. Note that a configuration is also well known in which the air intake conduit also serves as a conduit for insertion of a treatment instrument.

Japanese Patent Application Laid-Open Publication No. 2013-165791 discloses a configuration of an endoscope apparatus in which, by feeding gas frontward in a longitudinal axis direction of an insertion portion of an endoscope toward treatment target tissue from an opening portion of an air-feeding conduit formed around an objective lens on a distal end face of the insertion portion, suspended matters in a living body are prevented from adhering to the objective lens, and deterioration of an observation field of view is prevented.

SUMMARY OF THE INVENTION

A hood for endoscope according to one aspect of the present invention is attached to an endoscope, the endoscope including: an insertion portion configured to be inserted into a subject from a distal end side in a longitudinal axis direction; a distal end component member provided on the distal end side of the insertion portion and including an opening portion; and a conduit provided in the insertion portion and configured to cause an inside and an outside of the subject to communicate with each other via the opening portion; and the hood for endoscope including: a frame configured to be fitted to an outer circumference of the distal end component member; and a rectification member configured to, so that fluid spurted out forward in the longitudinal axis direction from the opening portion flows, changing an orientation in which the fluid flows, from the longitudinal axis direction to a circumferential direction of the frame intersecting the longitudinal axis direction by the fluid hitting the rectification member, guide the fluid in a direction not toward a position of the distal end component member provided with an observation member provided on the distal end component member and configured to observe the subject.

An endoscope system according to one aspect of the present invention is provided with: an endoscope including: an insertion portion configured to be inserted into a subject from a distal end side in a longitudinal axis direction; a distal end component member provided on the distal end side of the insertion portion and including an opening portion; and a conduit provided in the insertion portion and configured to cause an inside and an outside of the subject to communicate with each other via the opening portion; and a hood for endoscope attached to the endoscope, the hood for endoscope including: a frame configured to be fitted to an outer circumference of the distal end component member; and a rectification member configured to, so that fluid spurted out forward in the longitudinal axis direction from the opening portion flows, changing an orientation in which the fluid flows, from the longitudinal axis direction to a circumferential direction of the frame intersecting the longitudinal axis direction by the fluid hitting the rectification member, guide the fluid in a direction not toward a position of the distal end component member provided with an observation member provided on the distal end component member and configured to observe the subject.

BRIEF DESCRIPTION OF THE DRAWINGS

FIG. 6B is a partial perspective view showing a state in which the distal end portion to which the hood for endoscope is attached in FIG. 5 is inserted in the subject, and gas is fed from the air-feeding port;

DETAILED DESCRIPTION OF THE PREFERRED EMBODIMENTS

Embodiments of the present invention will be described below with reference to drawings. Note that the drawings are schematic and a relationship between a thickness and a width of each member, a thickness ratio among respective members and the like are different from actual ones. Among the mutual drawings, portions that are different in a mutual dimensional relationship and ratio are, of course, included.

First Embodiment

Figure 1:
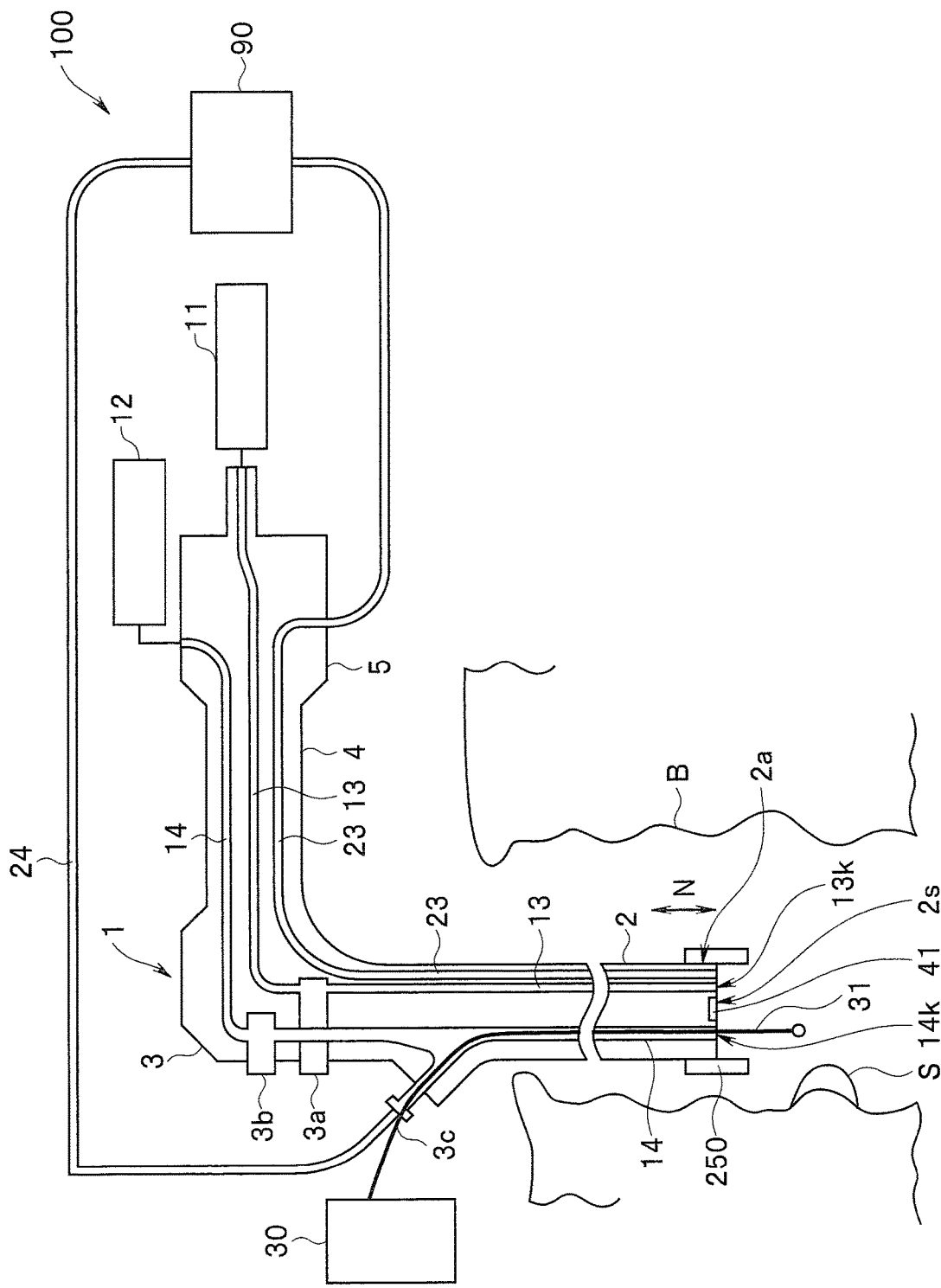
FIG. 1 is a diagram schematically showing a configuration of an endoscope system of a first embodiment.

FIG. 1 is a diagram schematically showing a configuration of an endoscope system of the present embodiment.

As shown in FIG. 1, a main part of an endoscope system 100 is configured with an endoscope 1 and a hood for endoscope 250 attached to the endoscope 1.

A main part of the endoscope 1 is configured being provided with an insertion portion 2 to be inserted into a subject B (a lumen of a living body, for example, a digestive tract) from a distal end side in a longitudinal axis direction N, an operation portion 3 provided being connected to a proximal end of the insertion portion 2, a universal cord 4 extended from the operation portion 3, and a connector 5 provided on an extension end of the universal cord 4, the connector being freely attachable to and detachable from an external apparatus.

In the endoscope 1, an air-feeding conduit 13 configured to cause an inside and an outside of the subject B to communicate with each other is provided, a distal end of the air-feeding conduit 13 being opened on a distal end face 2s of a distal end portion 2a, which is a distal end component member provided on the distal end side of the insertion portion 2 as an air-feeding port 13k which is an opening portion, and a proximal end of the air-feeding conduit 13 being opened on the connector 5. Note that the air-feeding conduit 13 is connected to an air-feeding pump 11 at the connector 5.

The air-feeding pump 11 is configured to supply a predetermined amount of gas into the subject B by an air-feeding switch 3a being switching-operated by an operator, the air-feeding switch 3a being provided on the operation portion 3 and configured to switch whether or not to feed air to the air-feeding conduit 13.

Further, in the endoscope 1, an air intake conduit 14 is provided, a distal end of the air intake conduit 14 being opened on the distal end face 2s as an air intake port 14k, a proximal end of the air intake conduit 14 being opened on the connector 5, and a part of the air intake conduit 14 being opened on a forceps port 3c on the operation portion 3.

Note that the air intake conduit 14 is connected to an air intake pump 12 at the connector 5. The air intake port 14k is not limited to being opened on the distal end face 2s but may be opened at a middle position of the insertion portion 2.

Furthermore, a high-frequency treatment instrument 31 of a cauterization apparatus 30 to be inserted into the subject B together with the insertion portion 2 is freely fittable to and removable from the air intake conduit 14 via the forceps port 3c.

A distal end side of the high-frequency treatment instrument 31 is projected into the subject B via the air intake port 14k and is used for treatment of a lesion site S on treatment target tissue in the subject B.

The air intake pump 12 is configured to send a predetermined amount of gas from inside the subject B to the outside of the subject by an air intake switch 3b being switching-operated by the operator on the operation portion 3, the air intake switch 3b being provided on the air intake conduit 14 and configured to switch whether or not to intake air by the air intake conduit 14.

In the endoscope 1, an air-feeding conduit 23 is provided, with a distal end of the air-feeding conduit 23 being opened on the distal end face 2s of the distal end portion 2a, and a proximal end of the air-feeding conduit 23 being configured to be opened on the connector 5 and cause an inside and an outside of the subject B to communicate with each other. The air-feeding conduit 23 is provided, for example, separately from the air-feeding conduit 13.

The air-feeding conduit 23 is connected to a circulation pump 90 at the connector 5.

The circulation pump 90 is connected to a controlling portion of an external apparatus (neither of the controlling portion nor the external apparatus is shown) and is configured to prevent suspended matters in the living body from adhering to an objective lens 41 described later and prevent deterioration of an observation field of view of the objective lens 41, by continuously supplying gas that is continuously sucked via air intake conduits 14 and 24, sent to the outside of the subject B and filtered, into the subject B via the air-feeding conduit 23 independently from the operator's operations, by operation control by the controlling portion.

The endoscope system 100 has the air intake conduit 24 a distal end of which is connected to the forceps port 3c and a proximal end of which is connected to the circulation pump 90.

In other words, the air intake conduit 24 branches from the air intake conduit 14 and is used as the air intake conduit 14 at least in the insertion portion 2. Note that the air intake conduit 24 may be, of course, provided separately from the air intake conduit 14.

The circulation pump 90 sucks gas including particles that prevents a field of view of the endoscope 1, the particles being generated by the high-frequency treatment instrument 31 of the cauterization apparatus 30 giving energy to the living body.

In other words, the circulation pump 90 is such that an air-feeding mechanism and a suction mechanism that are configured to filter gas sent from inside a subject and supply the gas into the subject again are integrated.

Figure 2:
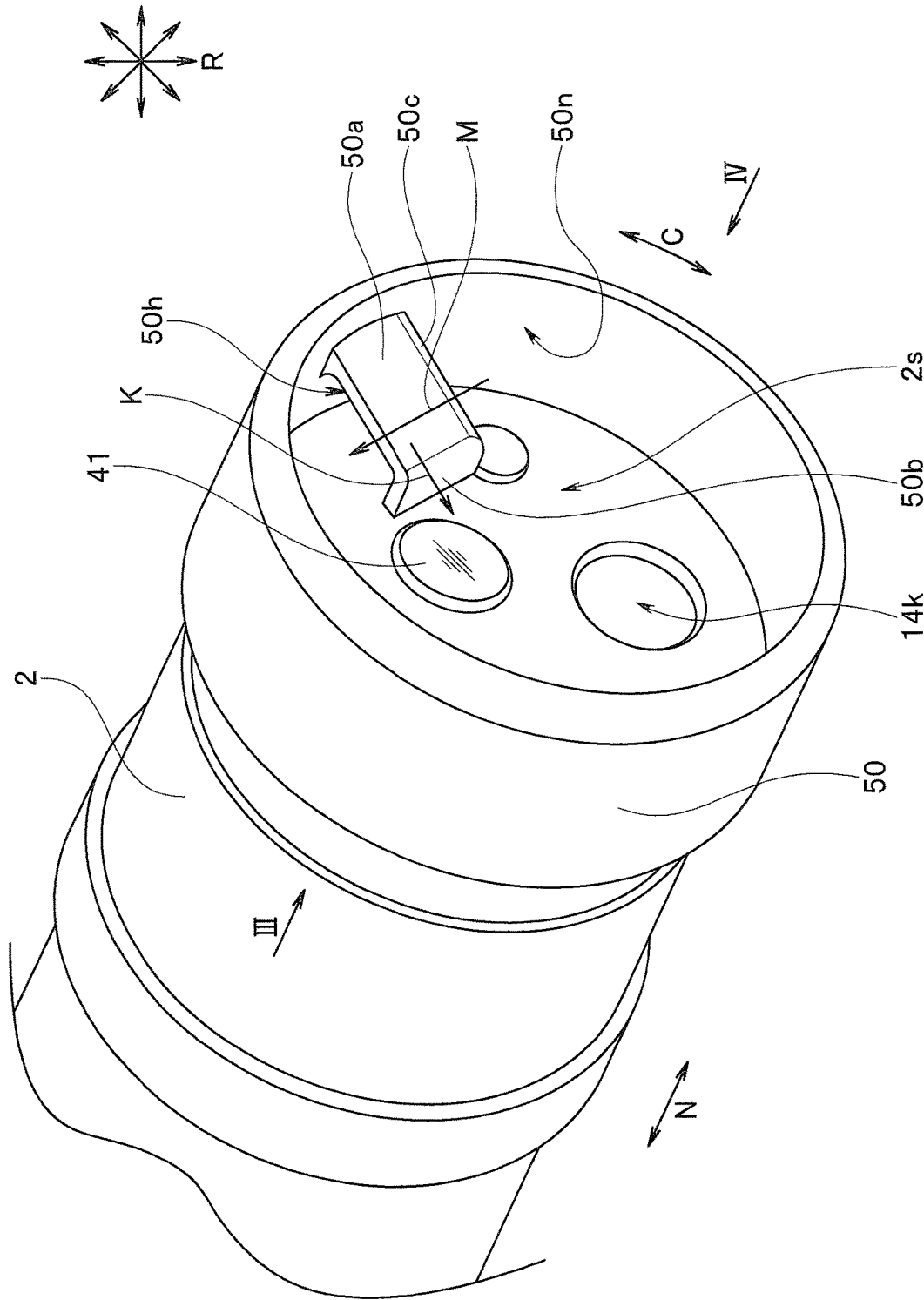
FIG. 2 is a partial enlarged perspective view in which a hood for endoscope is attached to a distal end portion of an insertion portion of an endoscope in FIG. 1.
Figure 3:
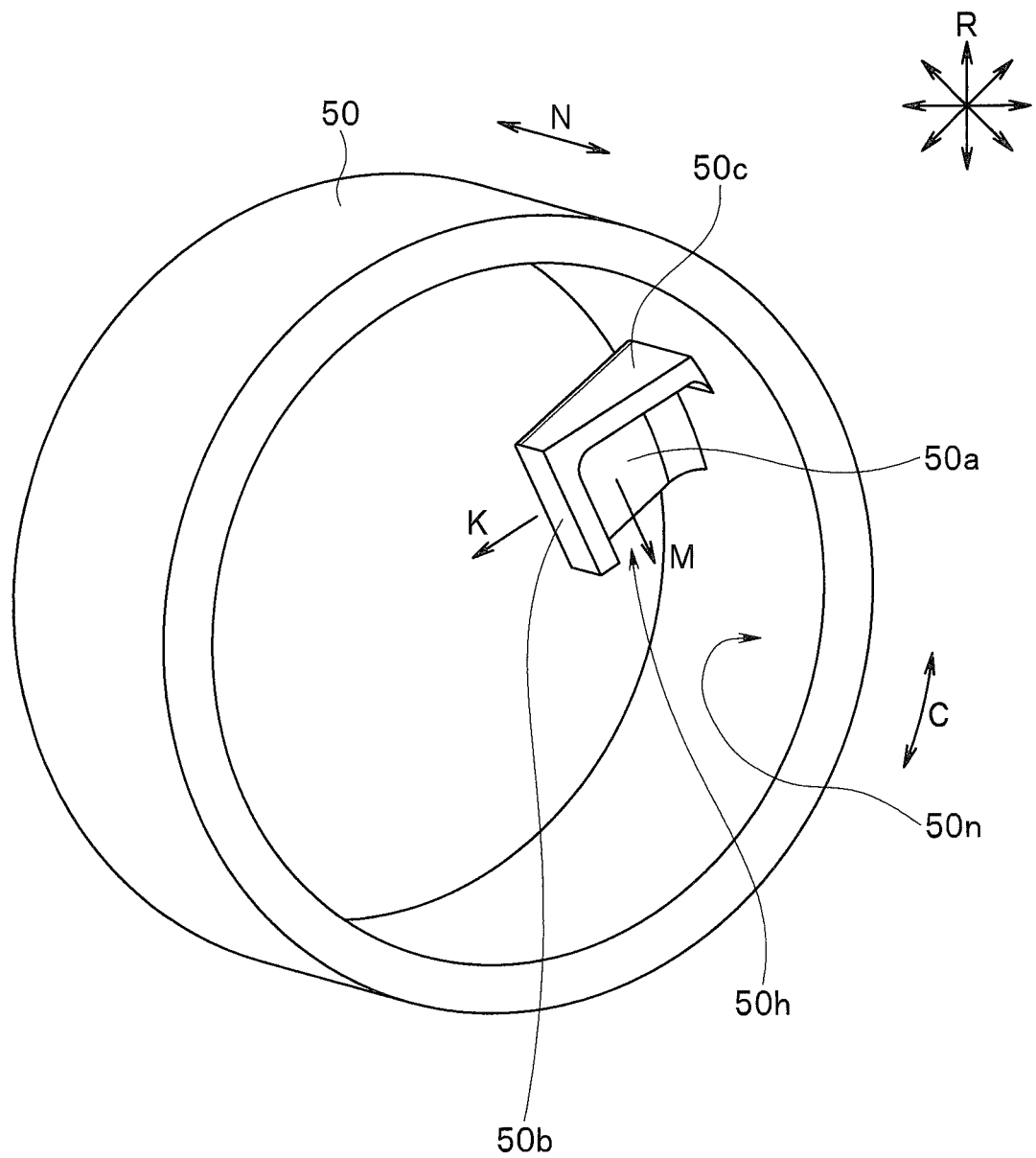
FIG. 3 is a perspective view when the hood for endoscope in FIG. 2 is seen in a III direction in FIG. 2.

Next, a configuration of the hood for endoscope 250 will be described using FIGS. 2 to 14. FIG. 2 is a partial enlarged perspective view in which the hood for endoscope is attached to the distal end portion of the insertion portion of the endoscope in FIG. 1; and FIG. 3 is a perspective view when the hood for endoscope in FIG. 2 is seen in a III direction in FIG. 2.

Figure 4:
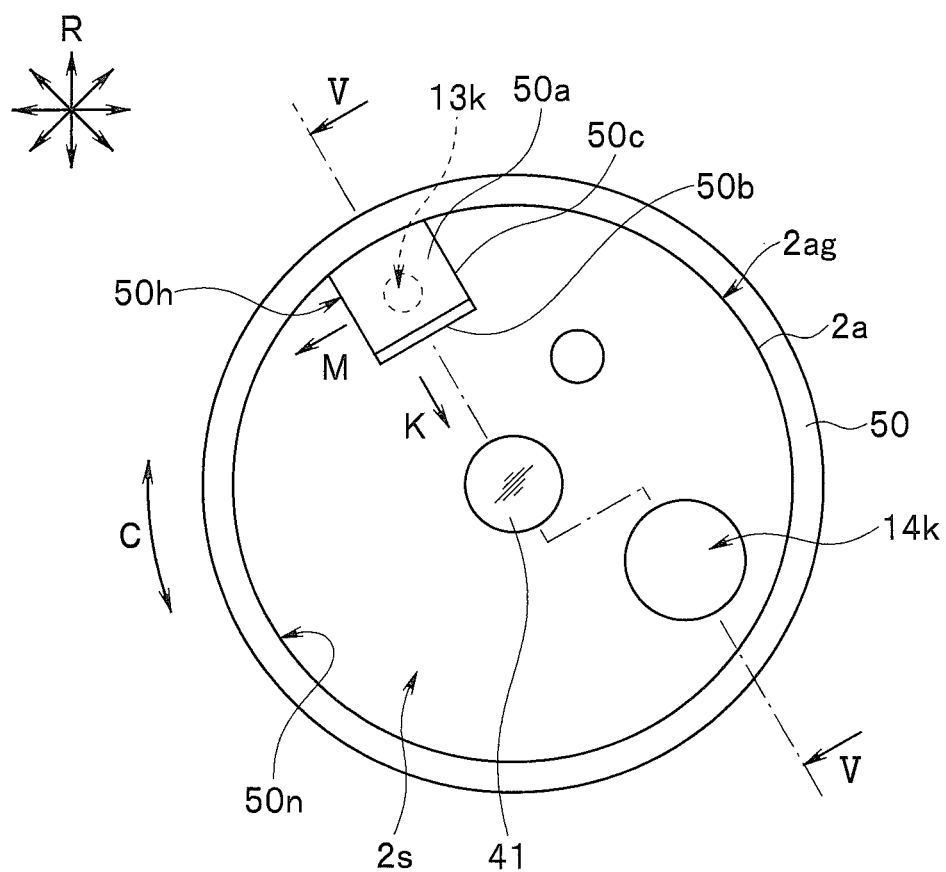
FIG. 4 is a front view when a distal end face and the hood for endoscope of the distal end portion of the insertion portion of the endoscope in FIG. 2 is seen in a IV direction in FIG. 2.
Figure 5:
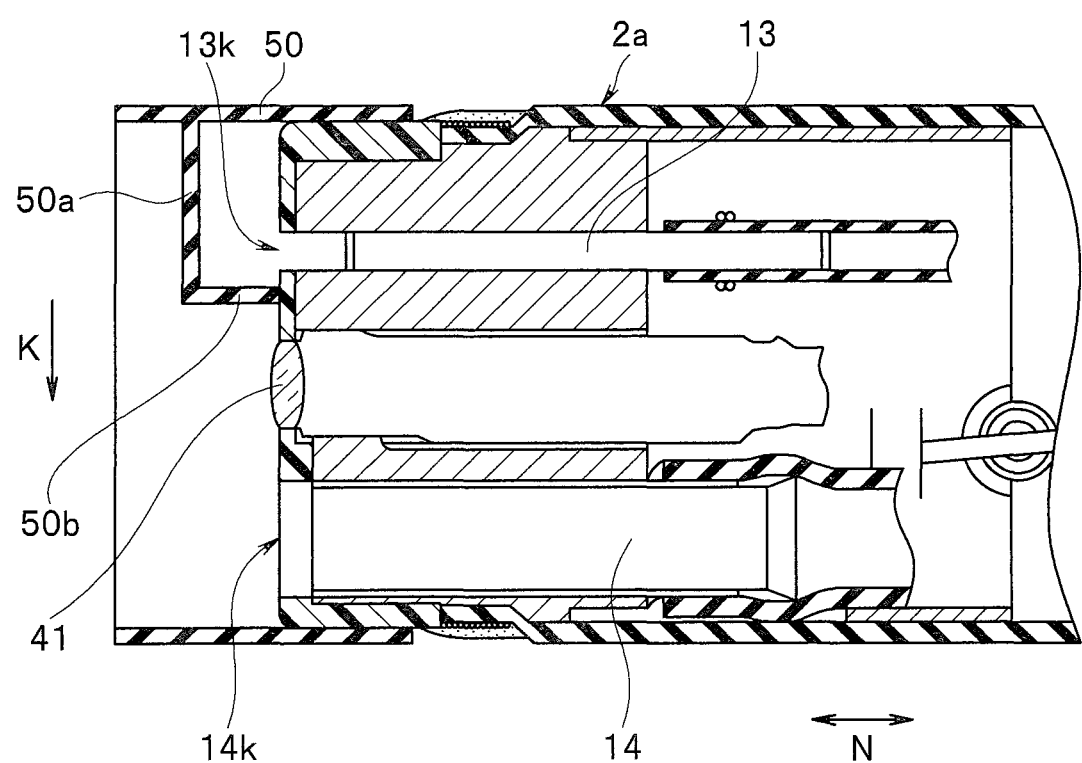
FIG. 5 is a partial cross-sectional view of the distal end portion and the hood for endoscope along a V-V line in FIG. 4.
Figure 6A:
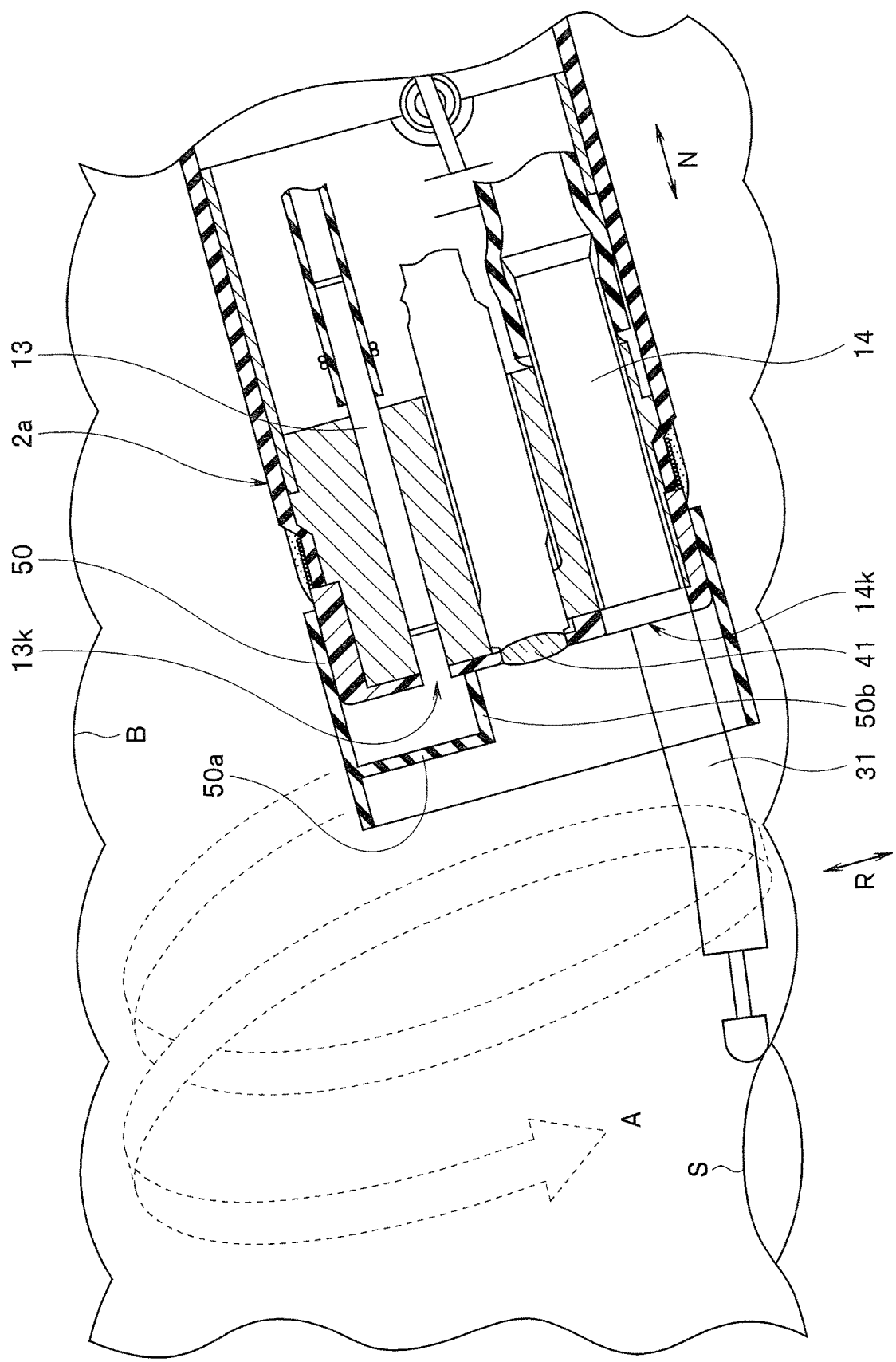
FIG. 6A is a partial cross-sectional view showing a state in which the distal end portion to which the hood for endoscope is attached in FIG. 5 is inserted in a subject, and gas is fed from an air-feeding port.

FIG. 4 is a front view when a distal end face and the hood for endoscope of the distal end portion of the insertion portion of the endoscope in FIG. 2 is seen in a IV direction in FIG. 2; FIG. 5 is a partial cross-sectional view of the distal end portion and the hood for endoscope along a V-V line in FIG. 4; FIG. 6A is a partial cross-sectional view showing a state in which the distal end portion to which the hood for endoscope is attached in FIG. 5 is inserted in a subject, and gas is fed from an air-feeding port; and FIG. 6B is a partial perspective view showing a state in which the distal end portion to which the hood for endoscope is attached in FIG. 5 is inserted in the subject, and gas is fed from the air-feeding port.

Figure 7:
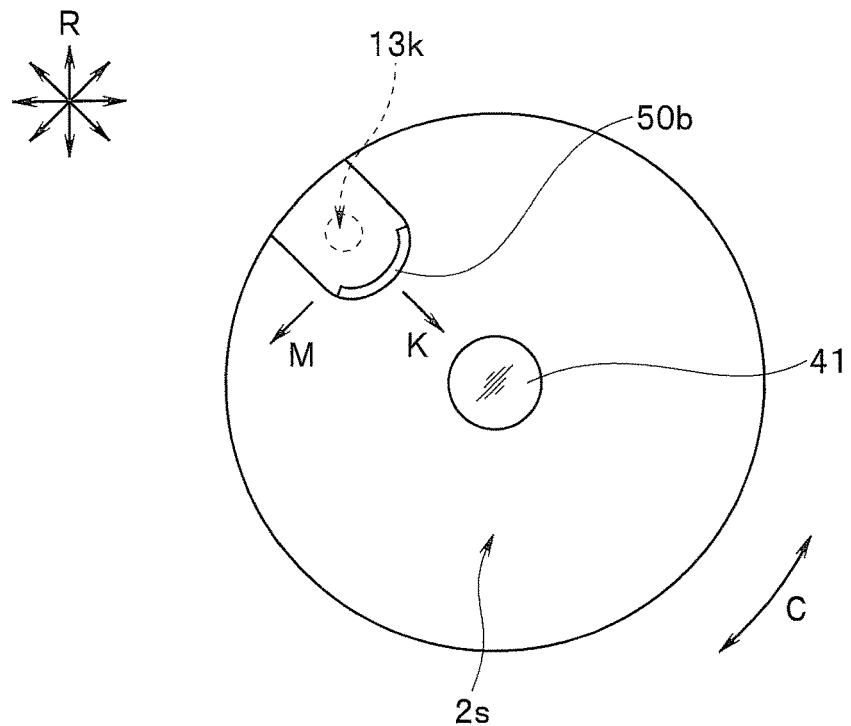
FIG. 7 is a front view of the distal end face of the distal end portion of the insertion portion showing a modification of a shape of a first rectification member in FIG. 2.
Figure 8:
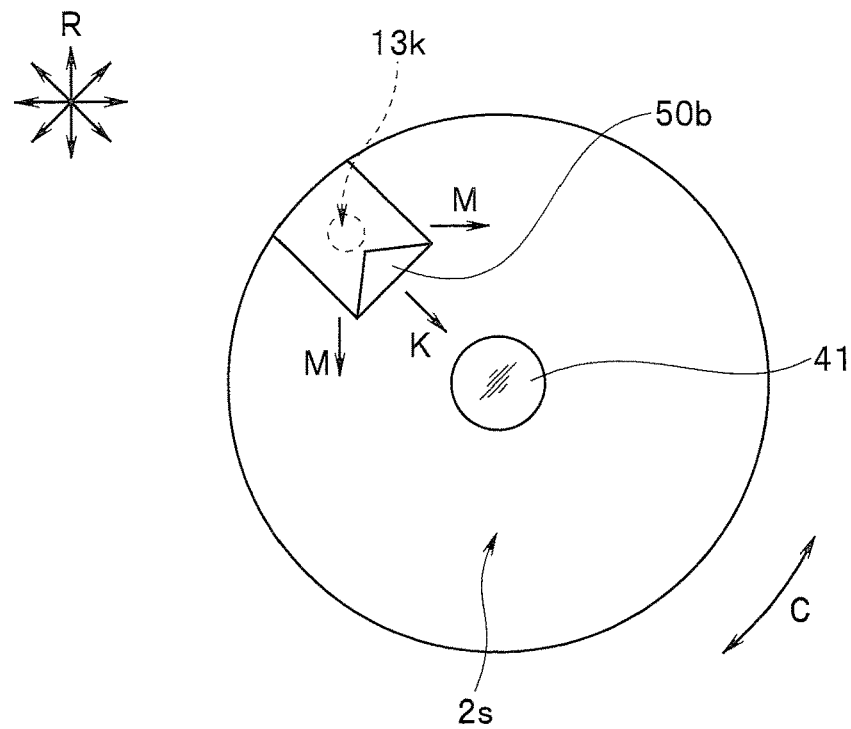
FIG. 8 is a front view of the distal end face of the distal end portion of the insertion portion showing a modification of the shape of the first rectification member in FIG. 2, the modification being different from the modification in FIG. 7.

FIG. 7 is a front view of the distal end face of the distal end portion of the insertion portion showing a modification of a shape of a first rectification member in FIG. 2; and FIG. 8 is a front view of the distal end face of the distal end portion of the insertion portion showing a modification of the shape of the first rectification member in FIG. 2, the modification being different from the modification in FIG. 7.

Figure 9:
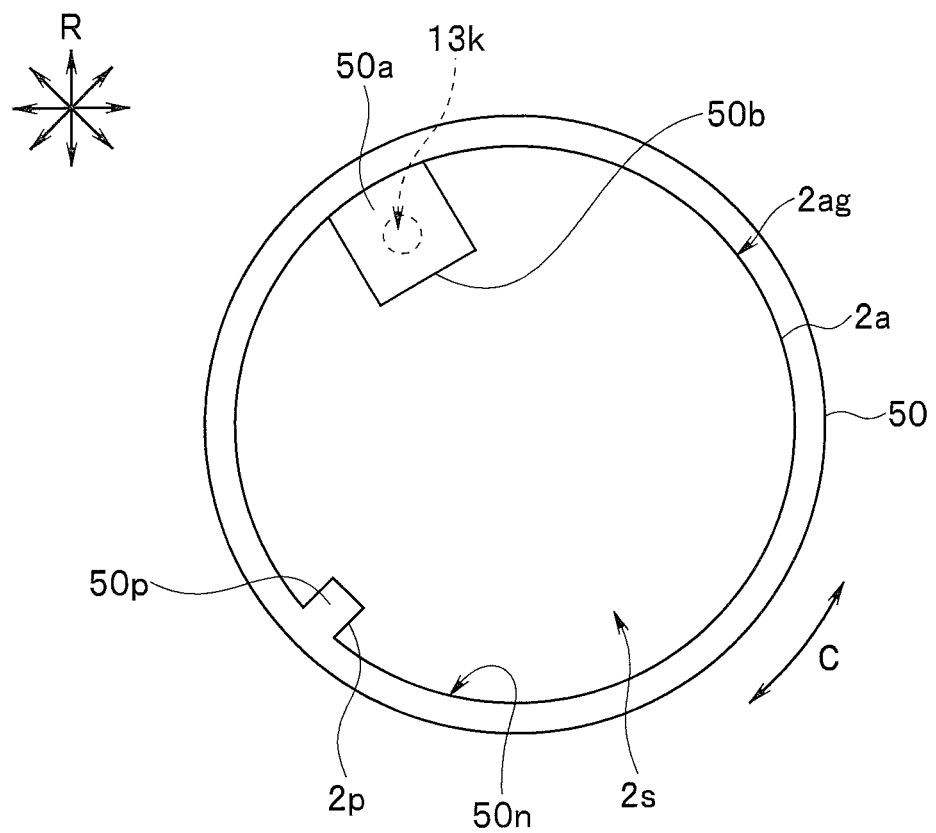
FIG. 9 is a front view showing a modification in which a recess portion is formed on an outer circumference of the distal end portion of the insertion portion of the endoscope in FIG. 2, and a projecting portion to be engaged with the recess portion is formed on an inner circumferential face of the hood for endoscope.
Figure 10:
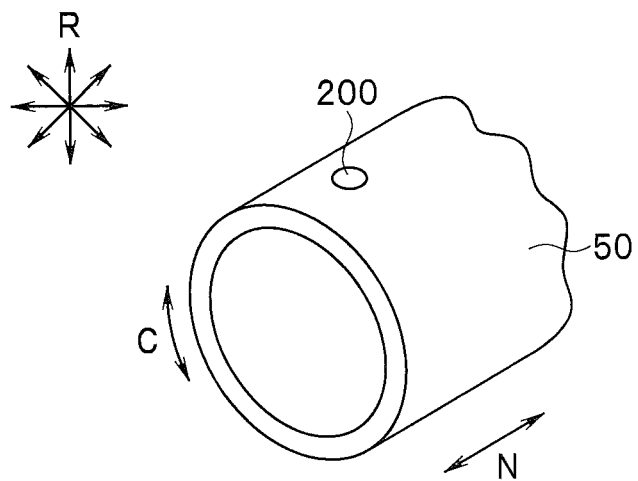
FIG. 10 is a perspective view showing a modification in which an indicator is provided on an outer circumferential face of the hood in FIG. 2.
Figure 11:
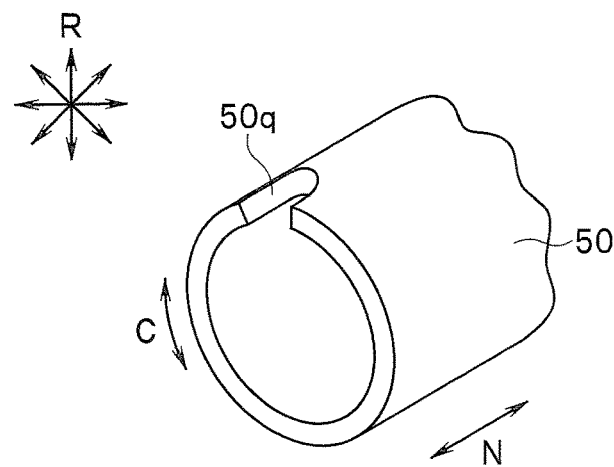
FIG. 11 is a perspective view showing a modification in which a notch is provided on the outer circumferential face of the hood in FIG. 2.

FIG. 9 is a front view showing a modification in which a recess portion is formed on an outer circumference of the distal end portion of the insertion portion of the endoscope in FIG. 2, and a projecting portion to be engaged with the recess portion is formed on an inner circumferential face of the hood for endoscope; FIG. 10 is a perspective view showing a modification in which an indicator is provided on an outer circumferential face of the hood in FIG. 2; and FIG. 11 is a perspective view showing a modification in which a notch is provided on the outer circumferential face of the hood in FIG. 2.

Figure 12:
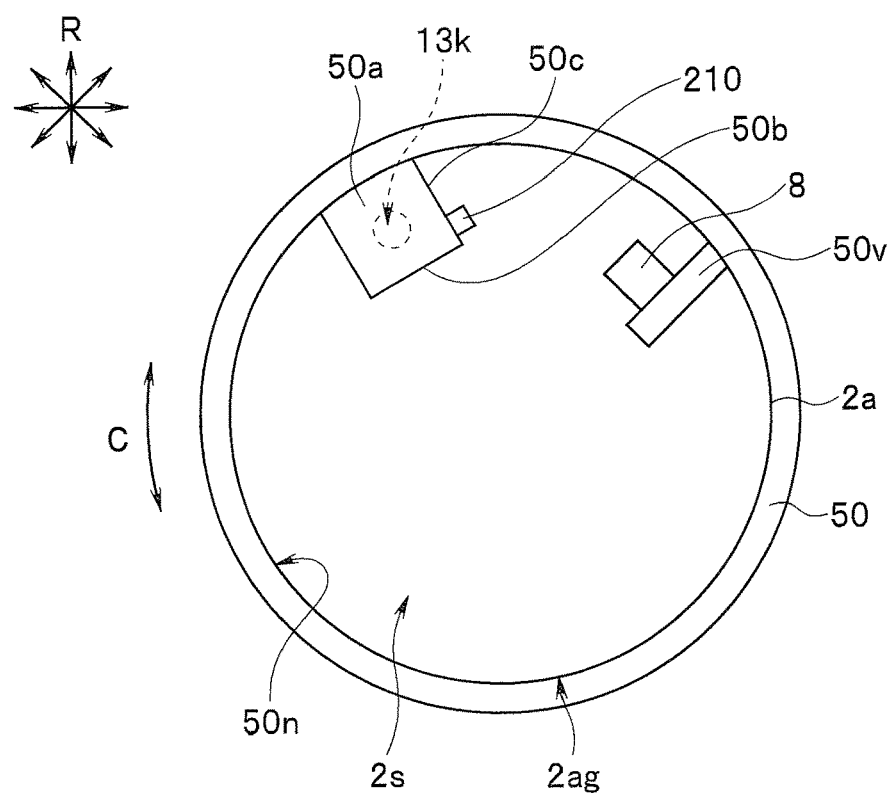
FIG. 12 is a front view showing a modification in which a projection for positioning of the hood for endoscope is provided on the distal end face of the distal end portion of the insertion portion of the endoscope in FIG. 2.
Figure 13:
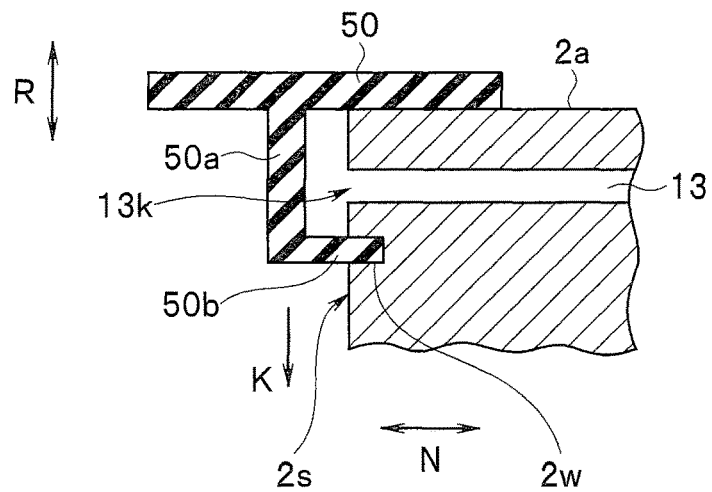
FIG. 13 is a partial cross-sectional view showing a modification in which a recess portion for positioning of the hood for endoscope is provided on the distal end face of the distal end portion of the insertion portion of the endoscope in FIG. 2.
Figure 14:
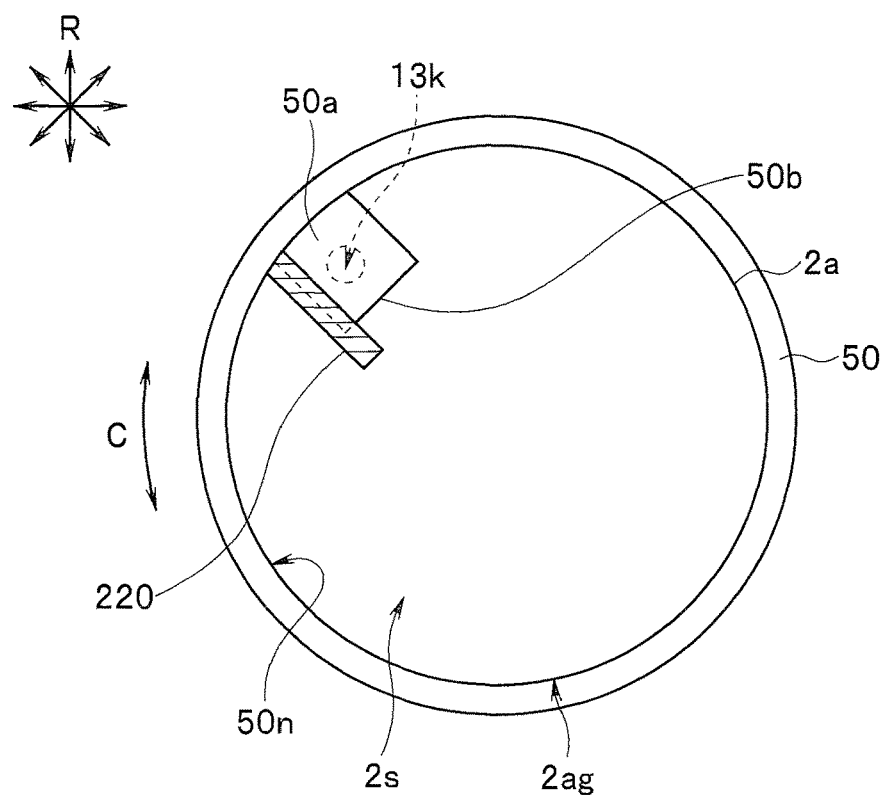
FIG. 14 is a front view showing a modification in which an indicator for positioning of the hood for endoscope is provided on the distal end face of the distal end portion of the insertion portion of the endoscope in FIG. 2.

FIG. 12 is a front view showing a modification in which a projection for positioning of the hood for endoscope is provided on the distal end face of the distal end portion of the insertion portion of the endoscope in FIG. 2; FIG. 13 is a partial cross-sectional view showing a modification in which a recess portion for positioning of the hood for endoscope is provided on the distal end face of the distal end portion of the insertion portion of the endoscope in FIG. 2; and FIG. 14 is a front view showing a modification in which an indicator for positioning of the hood for endoscope is provided on the distal end face of the distal end portion of the insertion portion of the endoscope in FIG. 2.

The hood for endoscope (hereinafter simply referred to as the hood) 250 is configured to, after being fitted to the distal end portion 2a, keep a distance constant between the objective lens 41, which is provided on the distal end face 2s and which is an observation member configured to observe an inside of a subject, and treatment target tissue, and at the time of turning over skin-like tissue of the lesion site S on the treatment target tissue taken off, for example, with the high-frequency treatment instrument 31, prevent the skin-like tissue from covering the lesion site S and cause the lesion site S to be exposed, in the cauterization treatment procedure such the ESD procedure described above.

As shown in FIG. 2, FIGS. 4 to 6A, and FIG. 6B, the hood 250 is provided with a frame 50 fitted to an outer circumference 2ag (see FIG. 4) of the distal end portion 2a.

As shown in FIG. 3, the frame 50 is formed in a tubular shape having a predetermined length in the longitudinal axis direction N, and a distal end and a proximal end are opened.

The frame 50 is fitted to the distal end portion 2a such that an inner circumferential face 50n is located at a part at least adjoining the air-feeding port 13k on the outer circumference 2ag of the distal end portion 2a.

On the inner circumferential face 50n of the frame 50, an opposing plate 50a, which is a first rectification member configured to change an orientation in which gas A flows, from the longitudinal axis direction N to a radial direction R of the distal end portion 2a, which is a direction intersecting the longitudinal axis direction N by causing the gas A, which is fluid spurted out forward in the longitudinal axis direction N from the air-feeding port 13k, to hit the opposing plate 50a, is provided such that the opposing plate 50a is located facing the air-feeding port 13k after the frame 50 is fitted to the distal end portion 2a. Note that the fluid is not limited to gas.

In other words, the opposing plate 50a is configured to prevent the gas A from being directly fed to the lesion site S located forward in the longitudinal axis direction N.

Rectification plates 50b and 50c, which are second rectification members configured to guide in a direction M the gas A the orientation of which has been changed by the opposing plate 50a, so that the gas A flows in a circumferential direction C of the frame 50, are provided in the radial direction R so as to face the inner circumferential face 50n, continuously following the opposing plate 50a.

Note that the rectification plate 50b is located between the air-feeding port 13k and the objective lens 41 on the distal end face 2s in the radial direction R after the frame 50 is fitted to the distal end portion 2a. In other words, the rectification plate 50b is configured to prevent the gas A from being directly fed to the objective lens 41.

A planar shape of the rectification plate 50b from forward in the longitudinal axis direction N may be any shape as long as the shape can prevent the gas A from being directly fed to the objective lens 41 as described above. For example, the rectification plate 50b may have a linear shape as shown in FIG. 4, a curved shape as shown in FIG. 7 or a triangular shape that equally divides the gas A, as shown in FIG. 8.

Furthermore, the rectification plate 50c is provided to feed the gas A spurted out from the air-feeding port 13k to the lesion site S in the subject B, the gas A drawing a spiral.

Here, in order to uniquely define a position to attach the frame 50 to the outer circumference 2ag of the distal end portion 2a in the circumferential direction C after the frame 50 is fitted to the distal end portion 2a, that is, in order to uniquely define the position to attach the frame 50 so that the inner circumferential face 50n of the frame 50 is located at the part at least adjoining the air-feeding port 13k on the outer circumference 2ag of the distal end portion 2a, and the opposing plate 50a and the rectification plates 50b and 50c are caused to face the air-feeding port 13k and the inner circumferential face 50n, respectively, as described above, a positioning portion may be provided on at least one of the distal end portion 2a and the frame 50.

More specifically, the position to attach the frame 50 in the circumferential direction C may be uniquely defined by a recess portion 2p, which is a positioning portion, being formed on the outer circumference 2ag of the distal end portion 2a, a projecting portion 50p, which is a positioning portion to be engaged with the recess portion 2p, being formed on the inner circumferential face 50n of the frame 50, and the projecting portion 50p being engaged with the recess portion 2p when the frame 50 is attached to the distal end portion 2a as shown in FIG. 9.

The position to attach the frame 50 in the circumferential direction C may be uniquely defined by an indicator 200, which is a positioning portion, being provided, for example, on an up direction side in the observation field of view of the objective lens 41 on the frame 50 and notifying a person who fits the frame 50 of an orientation of the frame 50 in the circumferential direction C on the frame 50 by the indicator 200 as shown in FIG. 10.

The position to attach the frame 50 may be uniquely defined by a notch 50q, which is a positioning portion, being provided, for example, on the up direction side in the observation field of view of the objective lens 41 on the frame 50 and notifying the person who fits the frame 50 of an orientation of the frame 50 in the circumferential direction C on the frame 50 by the notch 50q as shown in FIG. 11.

Note that the position to attach the frame 50 in the circumferential direction C may be uniquely defined by engaging the notch 50q with a projection or the like formed on the outer circumference 2ag of the distal end portion 2a.

The position to attach the frame 50 in the circumferential direction C may be uniquely defined by providing a projection 210, which is a positioning portion, on the distal end face 2s and causing the rectification plate 50c, which is a positioning portion, to be in contact with the projection 210 as shown in FIG. 12.

The position to attach the frame 50 in the circumferential direction C may be uniquely defined by causing a projection 50v, which is a positioning portion extended from the inner circumferential face 50n of the frame 50 in the radial direction R, to be in contact with a nozzle 8, which is a positioning portion configured to supply fluid to the objective lens 41 and provided on the distal end face 2s as shown in FIG. 12.

The position to attach the frame 50 in the circumferential direction C may be uniquely defined by providing a recess portion 2w, which is a positioning portion, on the distal end face 2s and causing a part of the rectification plate 50b, which is a positioning portion, to be engaged with the recess portion 2w as shown in FIG. 13.

The position to attach the frame 50 in the circumferential direction C may be uniquely defined by the person who fits the frame 50 adjusting an opening 50h so that the opening 50h is located at an indicator 220 which is a positioning portion formed on the distal end face 2s as shown in FIG. 14.

The configuration is not limited to the configurations shown in FIGS. 9 to 14. Any configuration is applicable as long as the configuration is a configuration that can uniquely define the position to attach the frame 50 to the distal end portion 2a in the circumferential direction C.

After the frame 50 is fitted to the distal end portion 2a, the rectification plates 50b and 50c form a closed space between the distal end portion 2a and the hood 250 excluding an opening portion 50k described later by being airtightly in contact with the distal end face 2s as shown in FIG. 5.

Note that at least one of the opposing plate 50a and the rectification plate 50c may be formed integrally with the frame 50.

The opposing plate 50a and the rectification plates 50b and 50c may be integrally formed. If the opposing plate 50a, the rectification plates 50b and 50c and the frame 50 are integrally formed, machining at the time of forming the hood 250 becomes easy, and the hood 250 can be disposable.

Of course, as for the opposing plate 50a and the rectification plates 50b and 50c, the opposing plate 50a and the rectification plates 50b and 50c which are separate bodies, respectively, may be integrally fixed, or each of the separate bodies may be fixed to the frame 50.

Each of the rectification plates 50b and 50c is configured to guide the gas A the orientation of which has been changed by the opposing plate 50a, in the direction M different from a direction K toward a position where the objective lens 41 is provided on the distal end face 2s, in the radial direction R.

More specifically, the rectification plates 50b and 50c are configured to guide the gas A in a direction along the inner circumferential face 50n of the frame 50.

Note that after the frame 50 is fitted to the distal end portion 2a, the opening 50h through which the gas A guided in the direction M different from the direction K by the rectification plates 50b and 50c passes is formed at a position facing the rectification plate 50c.

Therefore, after the gas A spurted out forward in the longitudinal axis direction N from the air-feeding port 13k hits the opposing plate 50a, and the orientation is changed to the radial direction R, the gas A is guided in the direction along the inner circumferential face 50n of the frame 50 by the rectification plates 50b and 50c via the opening 50h.

Note that even if it is assumed that the rectification plates 50b and 50c are not provided, it does not happen that the gas A is directly fed to the lesion site S from the air-feeding port 13k, due to the opposing plate 50a.

After that, by flowing through the inner circumferential face 50n, the gas A is fed forward in the longitudinal axis direction N, drawing a spiral shape in the subject B, as shown in FIGS. 6A and 6B, that is, a convection occurs in the subject B, and the above-stated mist generated at the time of cauterization treatment of the lesion site S using the high-frequency treatment instrument 31 is directly blown off.

Note that at this time, since the gas A is fed to the lesion site S, drawing a spiral shape, the gas A is fed to the lesion site S more softly than before, that is, the gas A is fed from the air-feeding port 13k on the endoscope distal end face to a lesion site linearly, and not directly but indirectly.

It has been shown that the rectification plate 50c is provided to supply the gas A to the lesion site S such that the gas A draws a spiral shape. However, even if the rectification plate 50c is not provided, that is, even if the opening 50k is formed at a position where the rectification plate 50c is provided, it is possible to prevent the gas A from being directly supplied to the lesion site S and the objective lens 41, by the opposing plate 50a and the rectification plate 50b, and it is possible to convect the gas A in the subject B.

Note that mist and the like blown off by supply of the gas A in the subject B is sucked by the air intake conduits 14 and 24 via the air intake port 14k.

Thus, in the present embodiment, it has been shown that the opposing plate 50a and the rectification plates 50b and 50c are provided on the frame 50 fitted to the outer circumference 2ag of the distal end portion 2a.

According to the above, the opposing plate 50a prevents the gas A spurted out from the air-feeding port 13k from being fed directly to the lesion site S; the rectification plate 50b prevents the gas A from being fed to the objective lens 41; and the rectification plates 50b and 50c guide the gas A in the direction along the inner circumferential face 50n of the frame 50 so that the gas A is fed to the lesion site S, drawing a spiral shape in the subject B which is a lumen of the living body or the like. Therefore, it does not happen that the lesion site S to which gas has been fed is deformed or vibrated or that mucus and the like around the lesion site S bubble due to feeding of gas as in a conventional case where the gas A is fed forward in the longitudinal axis direction N directly from the air-feeding port 13k. Therefore, it does not happen that treatability of the lesion site S using the high-frequency treatment instrument 31 is reduced or that the observation field of view of the objective lens 41 deteriorates.

Furthermore, since it does not happen that the gas A is directly supplied toward the objective lens 41, it does not happen that dirt filling in the subject B is sprayed to the objective lens 41.

Further, since a configuration capable of preventing deterioration of the observation field of view and decrease in treatability using the hood 250 that has been conventionally fitted to the outer circumference 2ag of the distal end portion 2a is provided, a diameter on the distal end side of the insertion portion 2 of the endoscope 1 is not increased as before.

From the above, it is possible to provide the hood for endoscope 250 and the endoscope system 100 that are provided with a configuration capable of preventing increase in the diameter on the distal end side of the insertion portion 2 of the endoscope 1 and securing a favorable observation field of view of the endoscope 1 at the time of cauterization treatment of treatment target tissue.

Second Embodiment

Figure 15:
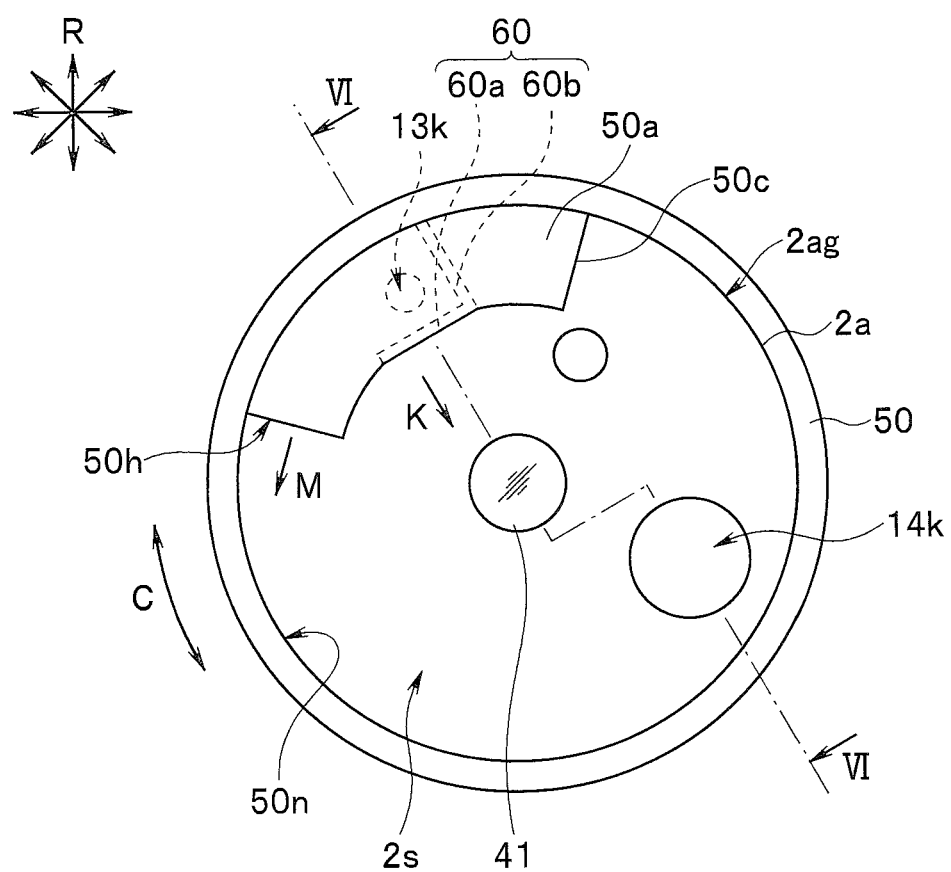
FIG. 15 is a front view of a distal end face and a hood for endoscope on a distal end portion of an insertion portion of an endoscope in an endoscope system of a second embodiment.
Figure 16:
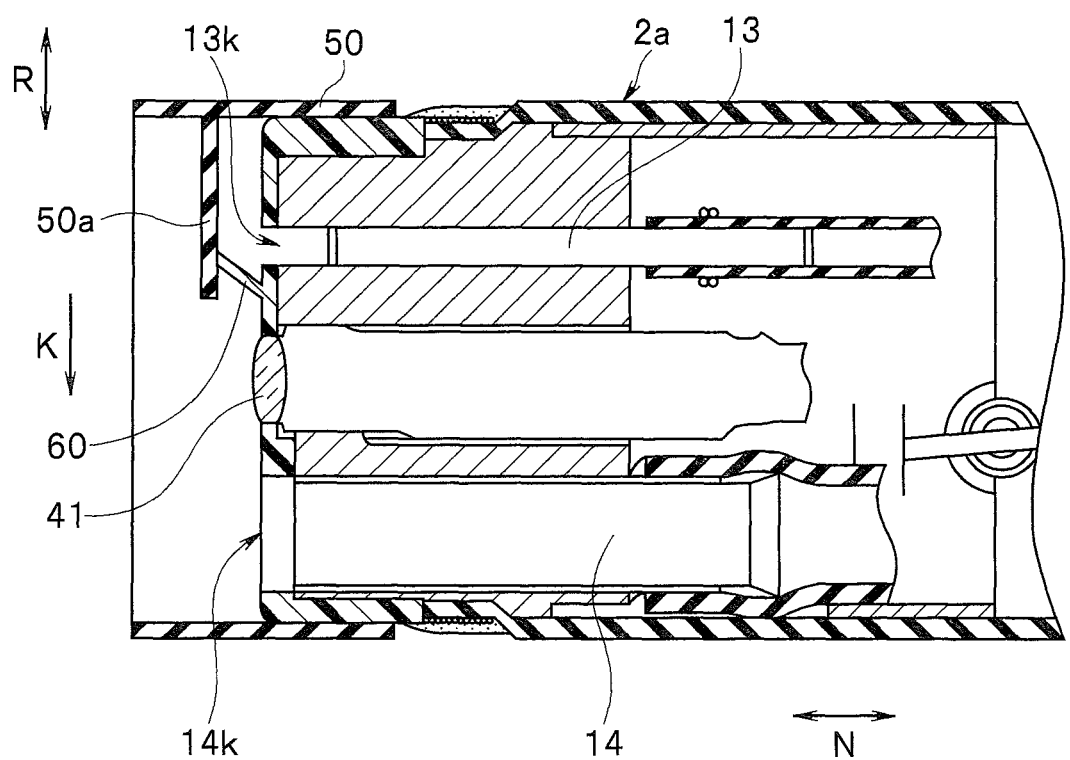
FIG. 16 is a partial cross-sectional view of the distal end portion and the hood for endoscope along a VI-VI line in FIG. 15.

FIG. 15 is a front view of a distal end face and a hood for endoscope on a distal end portion of an insertion portion of an endoscope in an endoscope system of the present embodiment; and FIG. 16 is a partial cross-sectional view of the distal end portion and the hood for endoscope along a VI-VI line in FIG. 15.

Configurations of the hood for endoscope and the endoscope system of the first embodiment shown in FIGS. 1 to 14 described above are different from configurations of the hood for endoscope and the endoscope system of the second embodiment in that an opposing plate is formed longer than in the first embodiment in a circumferential direction and that a projecting portion that is in contact with the opposing plate is provided on the distal end face of the distal end portion of the insertion portion of the endoscope.

Therefore, only the above different points will be described. The same reference numerals will be given to components similar to components in the first embodiment, and description of the components will be omitted.

As shown in FIGS. 15 and 16, in the present embodiment, the opposing plate 50a of the frame 50 is formed longer than in the first embodiment in the circumferential direction C.

The rectification plate 50b is not formed unlike the first embodiment. Instead, around the air-feeding port 13k on the distal end face 2s, a projecting portion 60 is provided which has a portion 60a projecting forward in the longitudinal axis direction N relative to other parts of the distal end face 2s and being in contact with the opposing plate 50a, and a portion 60b extending in the circumferential direction C.

In other words, by the projecting portion 60 and the opposing plate 50a, a closed space is formed between the distal end face 2 and the hood 250, excluding the opening 50k.

The projecting portion 60 has a function of guiding the gas A the orientation of which has been changed by the opposing plate 50a, in the circumferential direction C of the frame 50 together with the rectification plate 50c, similar to the rectification plate 50b.

Note that other components are similar to components in the first embodiment.

According to such a configuration, it is possible not only to obtain effects similar to the effects of the first embodiment described above but also to simplify the configuration of the hood 250 because of absence of the rectification plate 50*b*, that is, simplify the shape of the hood 250. Therefore, manufacturability of the hood 250 is improved.

Furthermore, by the opposing plate 50*a* being formed long in the circumferential direction C, positioning of the hood 250 against the distal end portion 2*a* in the circumferential direction C by the person who fits the hood 250, that is, positioning of the opposing plate 50*a* against the air-feeding port 13*k* becomes easier than in the first embodiment even if a positioning portion is not used.

Third Embodiment

Figure 17:
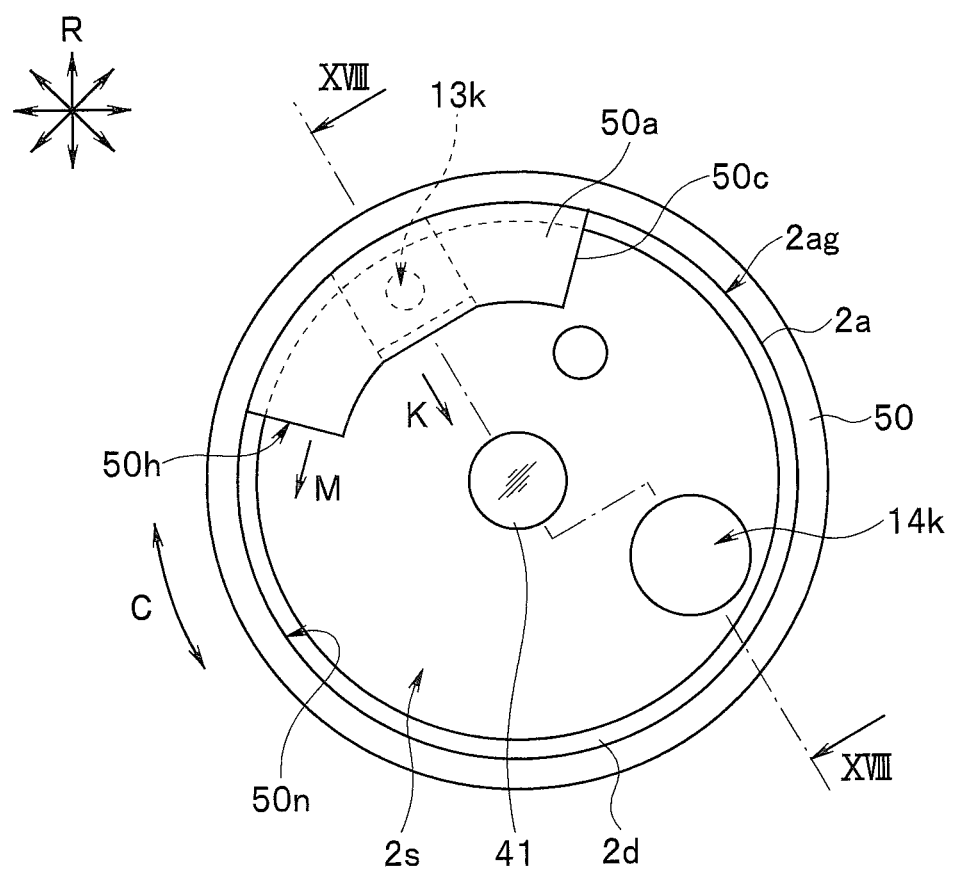
FIG. 17 is a front view of a distal end face and a hood for endoscope on a distal end portion of an insertion portion of an endoscope in an endoscope system of a third embodiment.
Figure 18:
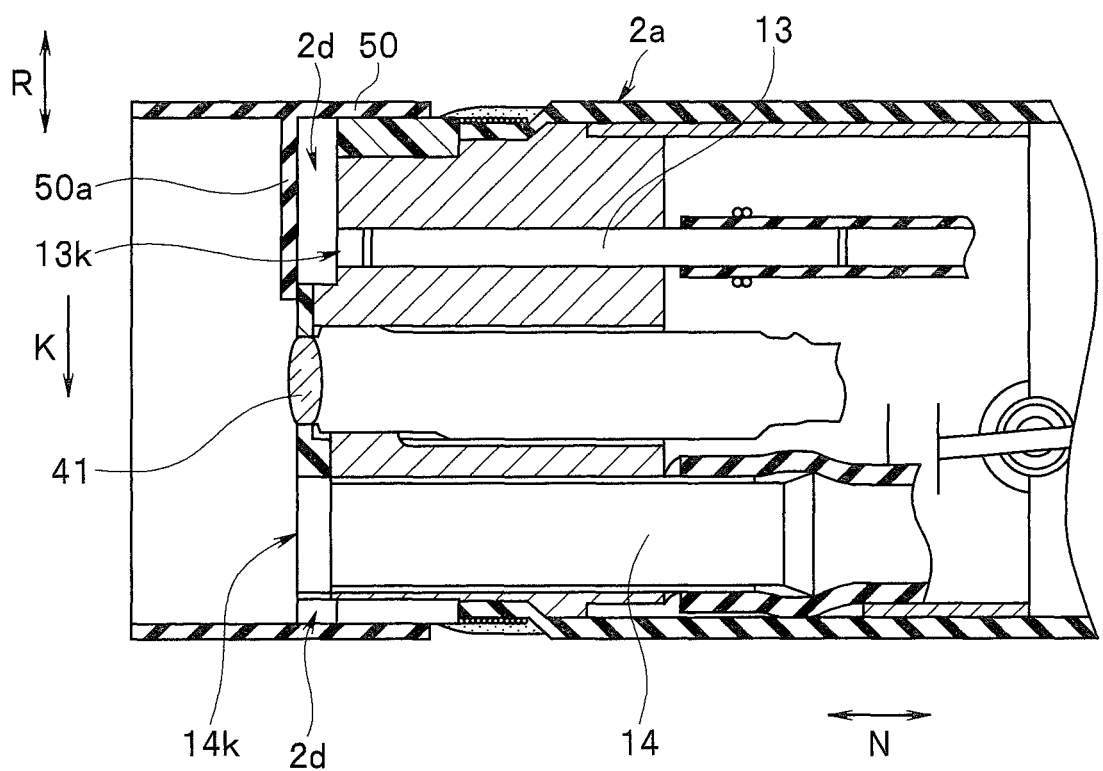
FIG. 18 is a partial cross-sectional view of the distal end portion and the hood for endoscope along a XVIII-XVIII line in FIG. 17.

FIG. 17 is a front view of a distal end face and a hood for endoscope on a distal end portion of an insertion portion of an endoscope in an endoscope system of the present embodiment; and FIG. 18 is a partial cross-sectional view of the distal end portion and the hood for endoscope along a XVIII-XVIII line in FIG. 17.

Configurations of the hood for endoscope and the endoscope system of the second embodiment shown in FIGS. 15 and 16 described above are different from configurations of the hood for endoscope and the endoscope system of the third embodiment in that a recess portion exposed on an outer circumference is formed instead of a projecting portion being formed on the distal end face of the distal end portion of the insertion portion of the endoscope.

Therefore, only the above different points will be described. The same reference numerals will be given to components similar to components in the second embodiment, and description of the components will be omitted.

As shown in FIGS. 17 and 18, in the present embodiment, a recess portion 2*d* recessed relative to other parts and exposed on the outer circumference 2*ag* is formed around the air-feeding port 13*k* on the distal end face 2*s*, for example, circumferentially in the circumferential direction C, instead of the projecting portion 60.

The recess portion 2*d* has a function of guiding the gas A the orientation of which has been changed by the opposing plate 50*a*, in the circumferential direction C of the frame 50 together with the rectification plate 50*c*, similar to the rectification plate 50*b*.

Note that in the present embodiment, when the frame 50 is fitted to the distal end portion 2*a*, the opposing plate 50*a* covers a front opening of the recess portion 2*d* by being in contact with the distal end face 2*s*.

In other words, by the distal end face 2*s* and the opposing plate 50*a*, a closed space is formed between the distal end face 2 and the hood 250, excluding the opening 50*k*.

According to such a configuration, it is also possible to obtain effects similar to the effects of the second embodiment described above. Additionally, since it is easier to form the recess portion 2*d* than to provide the projecting portion 60 on the distal end face 2*s*, manufacturability of the distal end portion 2*a* is improved.

Figure 19:
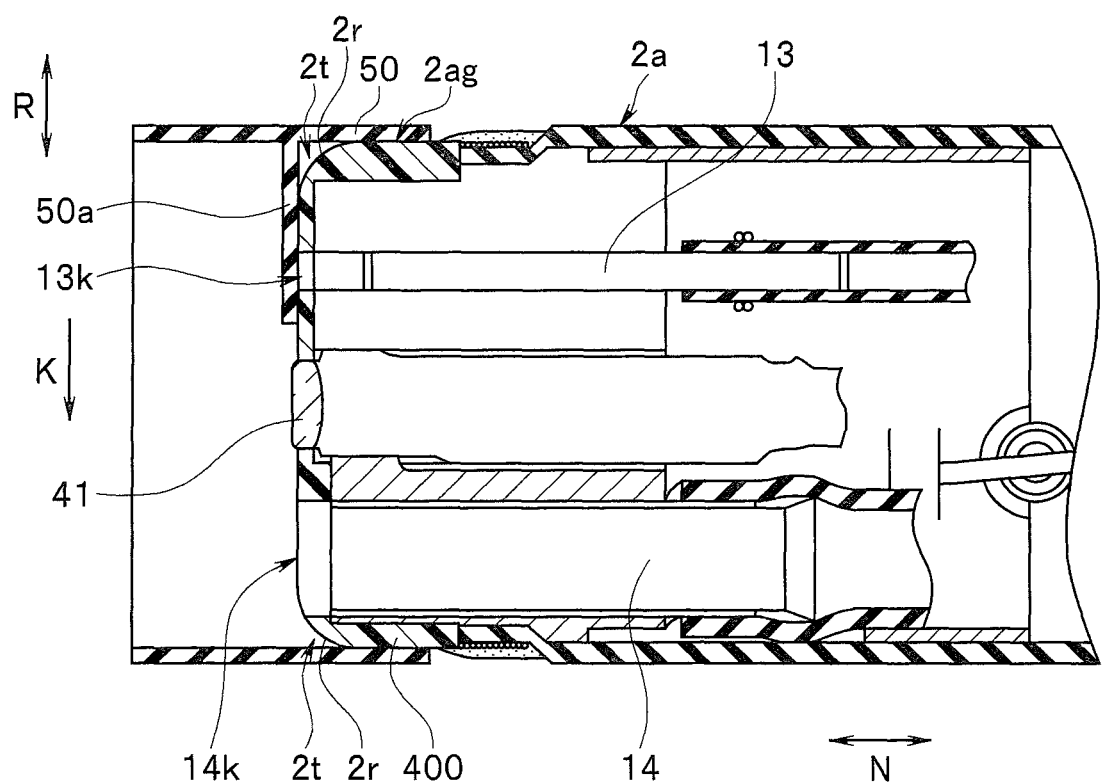
FIG. 19 is a partial cross-sectional view of the distal end portion and the hood for endoscope showing a modification in which a tapered face is formed on an outer circumference of the distal end face of the distal end portion in FIG. 18.

Note that a modification will be shown below using FIG. 19. FIG. 19 is a partial cross-sectional view of the distal end portion and the hood for endoscope showing a modification in which a tapered face is formed on an outer circumference of the distal end face of the distal end portion in FIG. 18.

As shown in FIG. 19, even if, for example, an arc-shaped tapered face 2*r* connecting to the outer circumference 2*ag* is formed in the circumferential direction C on an outer circumference of the distal end face 2*s* of the distal end portion 2*a*, more specifically, even if the tapered face 2*r* is formed on a distal end cover 400, a space 2*t* similar to the recess portion 2*d* is formed by the tapered face 2*r*, and, therefore, effects similar to the effects of the third embodiment described above can be obtained.

Furthermore, though a configuration having a first rectification member such as the opposing plate 50*a* configured to change an orientation in which fluid flows, from in the longitudinal axis direction N to in a direction intersecting the longitudinal axis direction N, by the fluid spurted out forward in the longitudinal axis direction N from an opening portion such as the air-feeding port 13*k* hitting the first rectification member, and second rectification members such as the rectification plates 50*b* and 50*c* configured to guide the fluid the orientation of which has been changed by the first rectification member so that the fluid flows in the circumferential direction C of the frame 50 has been described in the above embodiments, the configuration of a rectification member configured to change an orientation of fluid is not limited to what is configured with a plurality of portions as above.

Figure 20:
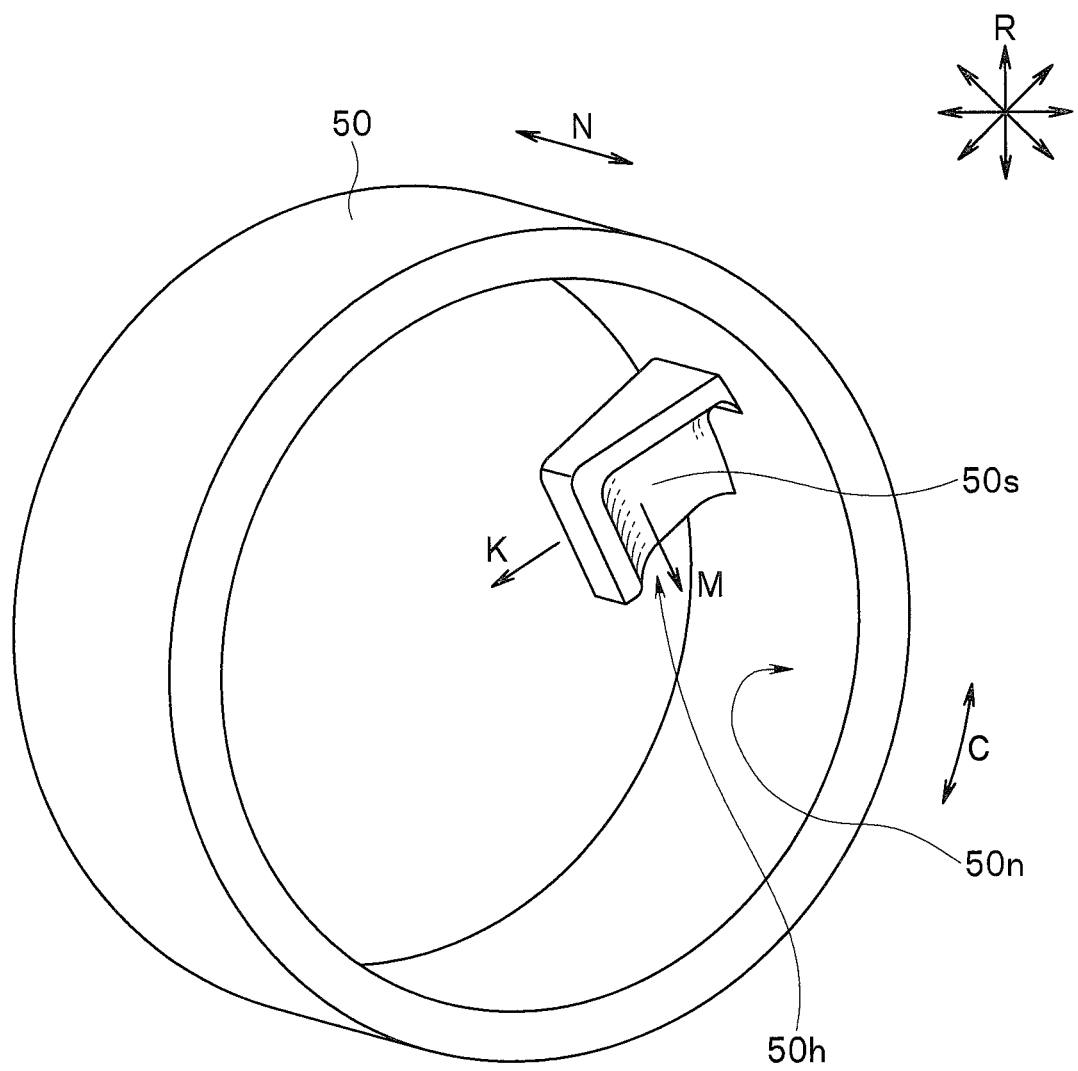
FIG. 20 is a perspective view of a modification in which the first rectification member and a second rectification member of the hood for endoscope in FIG. 3 are configured as one rectification member.

FIG. 20 is a perspective view of a modification in which the first rectification member and the second rectification member of the hood for endoscope in FIG. 3 are configured as one rectification member.

For example, as shown in FIG. 20, instead of providing each of the first rectification member and the second rectification member, a configuration is also possible in which one rectification member 50*s* configured to simultaneously play both of roles of the first rectification member and the second rectification member as such that guides fluid spurted out forward in the longitudinal axis direction N from an opening portion such as the air-feeding port 13*k* to flow, changing an orientation in which the fluid flows, from the longitudinal axis direction N to the circumferential direction C of the frame 50 intersecting the longitudinal axis direction N by the fluid hitting the rectification member 50*s*.

Thus, in the configuration where the rectification member 50*s* is provided, it is also possible to prevent fluid (the gas A) spurted out from the air-feeding port 13*k* from being directly fed to the lesion site S and the objective lens 41; it is possible to guide the gas A in the direction along the inner circumferential face 50*n* of the frame 50 so that the gas A is fed to the lesion site S, drawing a spiral shape in the subject B which is a lumen of the living body or the like; and it is possible to suppress deformation and vibration of the lesion site S to which gas has been fed and suppress mucus and the like around the lesion site S being bubbled by feeding of gas.

In other words, effects similar to the effects of the first to third embodiments, which make it possible to prevent decrease in treatability of the lesion site S using the high-frequency treatment instrument 31 and to prevent deterioration of the observation field of view of the objective lens 41, can be obtained.

What is claimed is:
1. A hood for an endoscope,
wherein the endoscope comprises:
an insertion portion having an insertion portion surface defining an opening through which a fluid flows from the insertion portion in a first direction; and
an optical element provided on the insertion portion surface, and
wherein the hood comprises:
a frame provided circumferentially around the first direction and extending along the first direction between a proximal side and a distal side of the frame; and
a plate surface extending from a portion of an inner circumferential surface of the frame between the proximal side and the distal side of the frame, wherein the plate surface defines at least one hood opening, and wherein the plate surface is configured to redirect the fluid flowing in the first direction through the opening of the insertion portion surface through the at least one hood opening in one or more directions towards the frame and away from the optical element.

2. The hood according to claim 1,
wherein the first direction is a longitudinal axis direction of the insertion portion,
wherein the frame is configured to be fitted to a distal end of the insertion portion and provided circumferentially around the longitudinal axis direction, and
wherein the frame is configured to guide the fluid redirected towards the frame in a direction along the inner circumferential surface of the frame.

3. The hood according to claim 1,
wherein at least a part of the plate surface is formed integrally with the frame.

4. The hood according to claim 1,
wherein the plate surface comprises:
a first plate configured to change an orientation of the fluid flowing in the first direction to a direction intersecting the first direction; and
a second plate configured to guide the fluid so that the fluid the orientation of which is changed by the first plate flows in a circumferential direction of the frame.

5. The hood according to claim 4,
wherein the second plate is configured to guide the fluid the orientation of which is changed by the first plate in a second direction and away from the optical element.

6. The hood according to claim 5,
wherein the first direction is a longitudinal axis direction of the insertion portion,
wherein the frame is configured to be fitted to a distal end of the insertion portion and provided circumferentially around the longitudinal axis direction, and
wherein the second plate is configured to guide the fluid in a direction along the inner circumferential surface of the frame.

7. The hood according to claim 4,
wherein the first plate and the second plate are integrally formed.

8. The hood according to claim 1, comprising a positioning portion configured to define a position to attach the frame to an outer circumference of a distal end of the insertion portion in a circumferential direction of the frame.

9. The hood according to claim 8,
wherein the positioning portion is configured to define the position to attach the frame to the distal end of the insertion portion so that the inner circumferential surface of the frame is located at a part at least adjoining the opening on the outer circumference of the distal end of the insertion portion, and
wherein the plate surface is configured to face the opening of the insertion portion.

10. An endoscope system comprising:
an endoscope comprising:
an insertion portion having an insertion portion surface defining an opening through which a fluid flows from the insertion portion in a first direction; and
an optical element provided on the insertion portion surface; and
a hood comprising:
a frame provided circumferentially around the first direction and extending along the first direction between a proximal side and a distal side of the frame; and
a plate surface extending from a portion of an inner circumferential surface of the frame between the proximal side and the distal side of the frame, wherein the plate surface defines at least one hood opening, and wherein the plate surface is configured to redirect the fluid flowing in the first direction through the opening of the insertion portion surface through the at least one hood opening in one or more directions towards the frame and away from the optical element.

11. The endoscope system according to claim 10,
wherein the plate surface comprises:
a first plate configured to change an orientation of the fluid flowing in the first direction to a direction intersecting the first direction; and
a second plate configured to guide the fluid so that the fluid the orientation of which is changed by the first plate flows in the circumferential direction of the frame.

12. The endoscope system according to claim 10, wherein the insertion portion comprises a recess portion around the opening, the recess portion being recessed relative to the insertion portion surface, and wherein the recess portion and the plate surface are configured to guide the fluid flowing through the opening in a circumferential direction of the frame.

13. The endoscope system according to claim 10, wherein the insertion portion comprises a projecting portion around the opening, the projecting portion projecting relative to the insertion portion surface and extending in a circumferential direction along the outer circumference of the insertion portion surface; and wherein the projecting portion and the plate surface are configured to guide the fluid flowing through the opening in a circumferential direction of the frame.

* * * * *